US007160686B1

(12) United States Patent
Erkhov

(10) Patent No.: US 7,160,686 B1
(45) Date of Patent: Jan. 9, 2007

(54) METHOD FOR PRODUCING A SPECIFIC ANTISERUM AGAINST THE UNIVERSAL TUMOROUS ANTIGEN AND METHOD FOR DIAGNOSING MALIGNANT TUMOURS USING SAID ANTISERUM

(75) Inventor: Valentin Sergeevich Erkhov, deceased, late of Moscow (RU); by Galina Mikhailivna Erkhova, legal representative, Moscow (RU)

(73) Assignee: Widnes Company Inc., Montevideo (UY)

( * ) Notice: Subject to any disclaimer, the term of this patent is extended or adjusted under 35 U.S.C. 154(b) by 0 days.

(21) Appl. No.: 09/673,686

(22) PCT Filed: May 18, 1998

(86) PCT No.: PCT/RU98/00143

§ 371 (c)(1),
(2), (4) Date: Jul. 25, 2001

(87) PCT Pub. No.: WO99/53952

PCT Pub. Date: Oct. 28, 1999

(30) Foreign Application Priority Data

Apr. 20, 1998 (RU) .................................. 98106976

(51) Int. Cl.
*G01N 33/53* (2006.01)
*G01N 33/48* (2006.01)
*G01N 33/564* (2006.01)
*G01N 33/559* (2006.01)

(52) U.S. Cl. .................. 435/7.1; 436/64; 436/520; 436/536; 436/515; 436/506

(58) Field of Classification Search ................ 436/64, 436/506, 515, 520, 536; 435/7.1; 530/387.2, 530/389.3, 389.6; 424/131.1, 173.1
See application file for complete search history.

(56) References Cited

FOREIGN PATENT DOCUMENTS

| EP | 0 058 616 A1 | 8/1982 |
|---|---|---|
| EP | 0 232 706 A2 | 8/1987 |
| FR | 2 482 309 | 11/1981 |
| SU | 1176886 | 9/1985 |
| SU | 1589215 | 9/1987 |
| SU | 1649443 | 2/1989 |
| SU | 1709220 | 4/1989 |
| SU | 1805392 | 4/1989 |
| SU | 1704087 | 7/1989 |
| SU | 2025734 | 9/1990 |
| SU | 2063768 | 8/1991 |
| SU | 2077725 | 3/1992 |
| WO | WO 97/22881 | * 6/1997 |

OTHER PUBLICATIONS

Beloglazova et al, Akusherstvo I Ginekogiia, 1995, vol. 5, pp. 33-44.*
Muraro et al, Cancer Research, 1985, vol. 45, pp. 5769-5780.*
Erkhov et al (Klinicheskaya Meditsina, 1995, pp. 33-34).*
Erkhov et al (Voprosy Onkologii, 1991, vol. 37, No. 6, pp. 751-754).*
The abstract of Kuo et al, Biorheology, 1994, 31, pp. 77-89.*
The abstract of Adamov et al, Klinicheskaya Laboratornaya Diagnostika, 1992, No. 3-4, pp. 23-25.*
The abstract of Rosenthal et al, Schweizerische Medizinische Wochenschrift, 1976, vol. 106, pp. 1116-1121.*
The abstract of Attansio et al, Molecular Immunology, 1990, vol. 27, pp. 513-522.*
X. Tuo et al., Cancer Research, vol. 52, No. 20, 1992, pp. 5744-5751.
D.L. Evans et al., Cancer Research, vol. 39, Nol. 6, Part 1, 1979, pp. 2006-2015.

* cited by examiner

*Primary Examiner*—Karen A. Canella
(74) *Attorney, Agent, or Firm*—Birch, Stewart, Kolasch & Birch, LLP

(57) ABSTRACT

The present invention pertains to the field of medicine and may be used for producing a specific antiserum as well as for carrying out immunological diagnoses of malignant tumours. This method for producing an antiserum involves sampling an embryo at the foetal stage from animals of a same genetic type so as to obtain a cell suspension. After immunization, this method involves sampling spleen cells from the animal, separating lymphocytes and immunizing the animal of the same genetic line using the lymphocyte suspension. An antiserum is then obtained and cells originating from healthy organs of the same animals are added to the antiserum. The mixture is finally decanted and the liquid located above the sediments is filtered. In order to carry out a diagnosis, the filtrate is added to the subject's blood and the results are obtained by immuno-fluorescence, by blood tests or using other methods of immunological diagnosis. It is thus possible to diagnose a tumour when the reliable values obtained differ from reference values.

6 Claims, No Drawings

METHOD FOR PRODUCING A SPECIFIC ANTISERUM AGAINST THE UNIVERSAL TUMOROUS ANTIGEN AND METHOD FOR DIAGNOSING MALIGNANT TUMOURS USING SAID ANTISERUM

CROSS REFERENCE TO RELATED APPLICAITONS

Applicant claims priority under 35 U.S.C. §119 of Russian Application No. 98106976 filed Apr. 20, 1998. Applicant also claims priority under 35 U.S.C. §120 of PCT/RU98/00143 filed May 18, 1998. The international application under PCT article 21 (2) was not published in English.

FIELD OF INVENTION

The present invention pertains to the field of medicine, particularly to oncology, its spheres and diagnosing malignant tumors.

BACKGROUND OF INVENTION

A brief review of immunodiagnosis in the oncology shows the following.

In 1949 it was first mentioned by L. A. Zilber and in 1957 it was proved by T. Pran and G. Main that malignant cells have their own antigens.

According to Abilev there are 4 groups of antigens.
1) Viral tumorous antigens. They are identical for any viral tumor of this type.
2) Carcinogenic tumorous antigens. They are individual for patients as well as for tumors.
3) Isoantigens of transplantation type or tumorous-specific transplantation antigens. They are different in all individual types of tumors, inducted by chemical agents. And they are the same in different tumors caused by the same virus.
4) Embryonic antigens.

During the process of carcinogenesis, cells are put to dedifferentiation, thus they acquire an embrional structure. In them there are to be found embryonic antigens, specific to embryonic development of organisms. These antigens can immunize the organism against tumors. The more studied antigens are the following: $\alpha$-fetoprotein and cancer embryonic antigen (CEA). The former is to be found by carcinoma of the liver, the latter—by adenocarcinmoma of the intestine, stomach, esophagus and pancreas.

Children having neuroblastoma, lymphosarcoma or tumor of the brain have $\alpha_2$—fetoprotein. Those who have carcinoma of the stomach have—fetal sulfoglycoprotein. The above mentioned antigens are localized inside the cell membrane or circulate in the blood.

There is a specific group of antigens, so called heterospecific antigens, existing. They could not be classified as heterologous to the organism, while besides tumors they exist in other normal tissues. Among heterospecific antigens there is a renal antigen, which exists as a norm in the kidney and in the tumor of liver—hepotoma.

Adenocarcinoma of kidney contains an antigen of lungs and liver.

The immunological diagnosis of malignant tumors based on indication in the subject's blood the above mentioned antigens, antibodies to them and on revealing sensitized to tumoral antigen lymfocytes.

Methods for diagnosing lymphosarcoma, neuroblastoma are based on revealing $\alpha$-fetoprotein. (On revealing antibodies to CEA—see Method in the Patent RU, 2077725, G. 01 N 33/53).

On revealing heterogenous antigens see Patent RU N 2063768, 1991, A 61K 39/00, Patent RU N 2025734, MPK G 01 N 33/53, author's certificate USSR N 170922, author's certificate N 1589215.

In the author's certificate N 1805392 (G 01 N 33/53) the method for diagnosing cancer by lymphocyte antigens ($H_{la-b}$ 35) is described.

In fact, no test of the existing level of diagnosis is universal. Revealing antibodies in blood is a less reliable test, for in human blood there is a very wide spectrum of antitumoral and tissue antibodies. There is no method existing for revealing specific universal tumors antigen.

In this field perspective is revealing sensitized lymphocytes which inhibit the growth of malignant cells. Though, they are active only against "their own" type of tumor.

Thus, the used methods for tumor immunological diagnosis do not satisfy in all respects the requirements of primary diagnosis of tumors, they are totally unsatisfactory in screening malignant neoplasms and groups of high risk. Therefore they may be used to a certain degree only in immunomonitoring healing of malignant tumors.

Failures in existing methods may be explained by the fact that the used antiserums against malignant tumorous antigens do not satisfy their own characteristics.

REVEALATION OF THE INVENTION

The aim of the Invention is producing antiserum against universal tumorous antigen, independent of tumor and organ type.

The prototype of the claimed method for producing specific antiserum as well as the method for diagnosis using the said antiserum is the method described in Patent RU N2063768, 1991, IPC, A 61 K 39/00. This method involves sampling tumor tissues from dead men, its freezing, obtaining a cell suspension, cell dispersion and decantation, extraction of antigens from supernatant fluid, extract immunization of animals, sampling blood from the immunized animals, obtaining the product from it, filling the specific antiserum into the reaction with the subject's blood, on the result of which a tumor is being diagnosed.

The claimed method unlike the well-known one allows obtaining antiserum for idtype of the T—cellular receptor functioning in malignant tumors. That is to obtain antiidotypic antiembrionic serum. That allows diagnosis of all types of tumors independently of their genesis and situs.

To accomplish the method for producing specific antiserum it is necessary to carry out two-stage immunization. That involves sampling an embryo at the foetal stage from animals of the same genetic type, dispersing it, obtaining cell suspension. Then the animal of the same genetic line is immunized by the cell suspension. After immunization it is necessary to sample spleen cells from the animal, to separate lymphocytes from the cell suspension at density gradient of 1,065–1,079. Using the above-mentioned lymphocytes it is necessary to accomplish multiple immunization of syngenic intact animals and then obtain antiserum from them using the standard method. This antiserum should be filtered (approximate diameter of pores in filters is 20 mcm).

The obtained antiserum has given reaction of precipitation with different types of tumors sampled from different people and in different organs.

It allowed devising methods for diagnosing malignant tumors on the basis of the obtained antiserum.

The well-known analogous methods for diagnosing tumors possess not high enough sensibility. Even the more effective among them have the sensibility level of not more than 40–60%. Such a low level of well-known oncologic immunodiagnostic tests can be explained so that the oncomarkers, used in said reactions, do not in fact satisfy their own characteristics. They are organo-specific or oncofetal antigens, characteristic of individual organisms or systems of organs in a norm. It leads to the following; an expected universal immunological expression of the only tumorformation mechanism pecularities is substituted by individual, characteristic of not tumoral conditions (inflammation, collagenosis).

Organo-specific antigens are well-known for being not binding for tumoral cell-transformation. That gives high percent of pseudopositive results by diagnosing malignant tumors.

The proposed method for revealing of the oncomarker strongly differs from the well-known ones by disclosing a universal highly specific antigenic marker of tumoral growth, preserving during the whole period of tumoral progression.

The method is based on the results of author's theoretical and experimental works establishing that in histologically different cells of malignant tumors there is a stable in tumoral progression process functioning, which recognizes superficial embryospecific antigens. The said mechanism is proved to be on the basis of tumor formation (immortalization and progress) phenomena.

To carry out the method for diagnosing tumors it is necessary to obtain the specific antiserum using the proposed method, to fill the antiserum against universal tumoral antigen into immunological reaction with the subject's tissues or physiologic fluid. After it the tumor is diagnosed by immuno-fluorescence or by blood tests. Tissues of tumor in immuno-fluorescence reaction or the subject's blood test can be used as tissues.

The tumor diagnosis is proved by statistically reliable differences of the reaction results between tentative and control tests.

By obtaining the blood test the following formula for calculating the differences between tentative and control tests should be used:

$$\alpha = \frac{\left|\left(A - \frac{B_1 + B_2}{2}\right)\right| \times X}{50}$$

where $\alpha$—diagnostic coefficient, if there is a tumor $\alpha \geq 1{,}5$

A—definition of blood test in tentative test (the antiserum for tumor antigen is added to the subject's citrated blood)

$B_1$ and $B_2$—definition of the blood test in control tests (the serum of the same animal, used for obtaining the antiserum, is added to the subject's citrated blood)

X—maxim definition of the blood test in the test A or the average $B_1$ and $B_2$ that is $$\frac{B_1 + B_2}{2}$$

Variants of Invention Accomplishment

An example of accomplishing methods for diagnosing malignant tumors.

At the foetal stage an embryo is sampled from Wister line rats, of 300–500 g. Weight. The embryo's tissues are dispersed in the medium 199 at the following correlation of volumes and tissue: medium 199 1:5. The obtained suspension is used for weekly immunization of the intact Wister line rats.

After a period of 1,5 month spleen cells are taken from the animals, dispersed and at the phyco-verografin gradient 1.065–1.079 lymphocytes are obtained.

From the said lymphocytes the suspension is obtained: medium 199 at the correlation 1;1, which is weekly put into other intact rats. After five immunizations the rats are killed, the blood is taken from them, "lightened", the antiserum is obtained from it, filtered. With the above mentioned antiserum the blood test was taken from the below mentioned groups of patients. To carry out the blood test the standard capillary with innerdiameter about 0,8 mm is used. 800 mcl of whole fresh venous blood, taken during the analysis, not late then 20 seconds after the moment of taking, is added to 200 mcl of 5%—sodium citrate bufer solution. The analysis should be carried out within 60 minutes since mixing the blood and the preservative. The analysis must not be taken in the case of hemolysis or coagulation. The said blood should be shared into 3 parts, 70 mcl each, the parts should be put into three separate test-tubes. One of the parts should be added with a tentative (with antibodies) serum, the two others should be added with a control (without antibodies) serum, 20 mcl each. The serums are to be filled directly into the blood with preservative, not on the walls. The capillaries should be of the same size. The mixtures are mixed and filled into the capillaries till the level mark 5/0. This way they are to be kept 60 minutes. 60 Minutes later the indices are to be read and calculated according to the above mentioned mathematic formula.

The antiserum, obtained by the said method using Wistar line rats, was used for diagnosing disease with certain patients.

In the blood test of a patient K., 1942 y.o., d-s: rectum carcinoma, the obtained results were the following:

$A=25$, $B_1=28$, $B_2=28$

According to the mathematic formula the coefficient $\alpha$ was calculated:

$$\alpha = \frac{\left|\left(25 - \frac{28 + 28}{2}\right)\right| \times 28}{50} = 1{,}7$$

$1{,}7 > 1{,}5$, that is diagnosis malignant tumor was proved.

In the blood test of a patient with fibroma of lobule of the auricle the results were the following:

$A=10$, $B_1=12$, $B_2=12$

According to the mathematic formula the α coefficient was calculated:

$$\alpha = \frac{\left|\left(10 - \frac{12+12}{2}\right)\right| \times 12}{50} = 0,48$$

α<1,5, that is diagnosis of benign tumor was proved.

Below there are the results of investigating a group of patients having malignant tumors.

Comedocarcinoma—125 patients

Sensibility—83,2%

Carcinoma of the lung—247 patients

Sensibility—98,1%

Carcinoma of the stomach—156 patients

Sensibility—85,2%

Carcinoma of the colon intestine—23 patients

Sensibility—82,5%

Carcinoma of the rectum intestine 27 patients

Sensibility—92,5%

Struma maligna—58% patients

Sensibility—79,5%

Carcinoma of the kidney—38 patients

Sensibility—78,6%

Carcinoma of the body of the womb—412 patients

Sensibility—75,0%

Carcinoma of the neck of the womb—41 patients

Sensibility—81,8%

Control group

Almost healthy—400 patients

Sensibility—5,1%

Mastopathia cystica-fibrotic—221 patients

Sensibility—8,3%

Gastritis—120 patients

Sensibility—6,2%

Gastric ulcer—62 patients

Sensibility—8,3%

Collagenosis—40 patients,

Sensibility—6,5%

Pneumonia—40 patients,

Sensibility 7,2%

(acute and chronic)

Prostatitis—18 patients,

Sensibility—2,1%

Chronic colitis—115 patients,

Sensibility—4,2%

INDUSTRIAL APPLICABILITY

Conclusion: The proposed method possesses sensibility not less than 92,4%, it is a highly effective diagnosing test.

In the application specific antiserum against universal tumoral antigen is the main component of the diagnosing device, on sale in Russia and abroad under the trade mark Turtest$^R$.

The invention claimed is:

1. A method for producing a specific anti-idiotypic anti-embryonic antiserum that specifically binds antigen-stimulated lymphocytes, comprising:
   i) performing a first immunization by immunizing a rat with a suspension of cells of tissue of a fetus of the same genetic line as the rat that is immunized;
   ii) recovering spleen cells from said immunized rat and separating lymphocytes therefrom, thus obtaining a lymphocyte suspension;
   iii) performing a second immunization by immunizing a rat of the same genetic line as the rat that is first immunized with said lymphocyte suspension;
   iv) recovering an antiserum from said rat immunized in the second immunization;
   v) adding cells of whole organs of kidney, lung and liver of a normal rat of the same genetic line as the immunized rat to said antiserum, forming a suspension; and
   vi) separating the supernatant from the sediments from the obtained suspension to obtain the anti-idiotypic anti-embronic antiserum that specifically binds antigen-stimulated lymphocytes.

2. The method according to claim 1, in which the separation of the supernatant from the sediments is carried out by filtration.

3. The method of claim 1, in which the second immunization is performed as repeated administrations of the cell suspension over an interval of time.

4. A method for diagnosis of a malignant tumor comprising:
   i) performing a sample test by:
      a) contacting an antiserum obtained by the method of claim 1, 2 or 3 with a sample of blood of a human subject to be examined, and
      b) detecting binding of the antiserum to the sample; and
   ii) determining the presence of a malignant tumor by deviation of the test results from a control test.

5. The method according to claim 4, in which the method of immunodetection is an immuno-fluorescence test or an erythrocyte sedimentation test.

6. The method according to claim 4, in which an erythrocyte sedimentation test is used and a diagnosis of the presence of a malignant tumor is made when α is greater than or equal to 1.5 and $$\alpha = \frac{\left|\left(A - \frac{B_1 + B_2}{2}\right)\right| \times X}{50}$$

wherein:
A is the index of the ESR of sample test,
$B_1$ and $B_2$ are indices of the ESR of tests upon control samples,
X is the maximum value of the ESR observed in the test.

* * * * *